United States Patent [19]

Benziger

[11] Patent Number: 4,481,371
[45] Date of Patent: Nov. 6, 1984

[54] METHOD OF MAKING FINE-GRAINED TRIAMINOTRINITROBENZENE

[75] Inventor: Theodore M. Benziger, Santa Fe, N. Mex.

[73] Assignee: The United States of America as represented by the United States Department of Energy, Washington, D.C.

[21] Appl. No.: 517,531

[22] Filed: Jul. 26, 1983

[51] Int. Cl.$^3$ ...................... C07C 85/00; C07C 85/26
[52] U.S. Cl. ....................................... 564/406; 149/92
[58] Field of Search ........................................ 564/406

[56] References Cited

U.S. PATENT DOCUMENTS 3,002,998  10/1961  Kaplan et al. ....................... 564/406
4,032,377   6/1977  Benziger ............................. 564/406

OTHER PUBLICATIONS

Locke, "Low Chlorine TATB Produced by Emulsion Amination", Mason & Hanger-Silas Mason Co., Inc., Report No. MHSMP-80-14, 1980.

*Primary Examiner*—Paul F. Shaver
*Attorney, Agent, or Firm*—William A. Eklund; Paul D. Gaetjens; Michael F. Esposito

[57] ABSTRACT

A method of forming a fine-grained species of the insensitive high explosive sym-triaminotrinitrobenzene (TATB) without grinding. In accordance with the method, 1,3,5-trichloro-2,4,6-trinitrobenzene (TCTNB) is aminated by reaction with gaseous ammonia in an emulsion of toluene in water. The ratio of water to toluene in the emulsion is selected so that toluene is the dispersed phase in the emulsion. The size of the dispersed TCTNB-containing toluene droplets determines the particle size of the resulting TATB. The emulsion is preferably formed with an emulsifier such as ammonium oleate, which may be generated in situ from oleic acid, and stabilized with a protective colloid such as polyvinyl alcohol.

8 Claims, No Drawings

METHOD OF MAKING FINE-GRAINED TRIAMINOTRINITROBENZENE

This invention is the result of a contract with the Department of Energy (Contract No. W-7405-ENG-36).

BACKGROUND OF THE INVENTION

The present invention is generally related to high explosives. More particularly, the present invention is related to the manufacture of the insensitive high explosive sym-triaminotrinitrobenzene (TATB).

Sym-triaminotrinitrobenzene (TATB) is a high explosive characterized by high thermal stability and extreme insensitivity. These characteristics make it highly desirable in applications where the prevention of accidental detonation is a primary consideration.

A method of producing high-purity TATB has been previously disclosed in the U.S. Pat. No. 4,032,377 to Theodore M. Benziger, inventor of the present invention. In accordance with that method, TATB is prepared by the reaction of ammonia with 1,3,5-trichloro-2,4,6-trinitrobenzene (TCTNB) in a solvent consisting of toluene containing a small amount (on the order of 2%) of water. TATB has also been made by the simple amination of TCTNB in toluene, as described for example in the U.S. Pat. No. 3,985,595, also to Benziger. As discussed in the '377 patent, the advantage of incorporating a small amount of water in the toluene solvent is that the resulting TATB is substantially free of occluded ammonium chloride, which is a byproduct of the amination reaction.

As noted above, TATB is notable for and is most often employed on account of its superior insensitivity to detonation. In certain applications, however, such as in explosive initiators and explosive boosters, the insensitivity of TATB is in fact too high to ensure optimum performance reliability. Accordingly, methods have been sought for increasing the sensitivity of TATB. In this regard, it has been generally known that the sensitivity of solid explosives can be increased by decreasing the particle size of the material and correspondingly increasing the surface area per unit weight of the material. One obvious method of reducing the particle size of TATB is by grinding; however, as with all high explosives this is an undesirable approach because it can be a hazardous procedure.

It is also generally recognized that the degree of uniformity of particle size in an initiating-type explosive is a factor that affects the detonation characteristics of the explosive. Accordingly, it has been generally sought to provide methods of making such explosives with a controlled, small particle size.

SUMMARY OF THE INVENTION

Accordingly, it is the object and purpose of the present invention to provide a method of making fine-grained TATB.

It is also an object of the present invention to provide a method of producing TATB having increased sensitivity over TATB produced by previously known methods.

It is another object of the present invention to provide a method of producing fine-grained TATB, which method does not require grinding of the TATB as a final step.

It is yet another object to provide a method of making TATB having a small and uniform particle size.

Additional objects, advantages and novel features of the invention are set forth in part in the following description, and in part will become apparent to those skilled in the art upon consideration of the following description or by practice of the invention. The objects and advantages of the invention may be realized and attained by means of the methods particularly pointed out in the appended claims.

To achieve the foregoing and other objects, and in accordance with the purposes of the present invention as embodied and broadly described herein, the method of the present invention comprises the amination of TCTNB while dissolved in an emulsion of an organic solvent, preferably toluene, in water. The emulsion includes a protective colloid, and is prepared with the water volume being greater than the toluene volume, so that the water is the continuous phase and the toluene is the dispersed phase of the emulsion. Amination is preferably conducted by introducing gaseous ammonia into the emulsion. The particle size of the product TATB is effectively controlled by the size of the toluene droplets in the emulsion.

In accordance with other aspects of the invention, the reaction emulsion is prepared with an emulsifying agent, for example ammonium oleate, which can be formed in situ by the reaction of oleic acid with the gaseous ammonia.

These and other aspects of the invention will be apparent from the following more detailed description of the invention.

DETAILED DESCRIPTION OF THE INVENTION

It will be understood that an emulsion of the type discussed herein generally consists of two mutually immiscible liquids which are intimately intermixed to form a homogeneous dispersion. One liquid, which is generally the liquid present in the greatest volume, forms a continuous phase. The other liquid is dispersed as small droplets throughout the continuous phase of the first liquid. In the present invention, the TCTNB, which is to be aminated to form TATB, is insoluble in water and is soluble in toluene. Consequently, in an emulsion consisting of toluene droplets dispersed in water, TCTNB added to the emulsion will reside in the toluene droplets. The size of the TCTNB-containing toluene droplets determines the maximum size of the TATB particles that are formed upon the amination of the TCTNB.

In the prior art method described in U.S. Pat. No. 4,032,377, referenced above, water is the dispersed phase (constituting approximately 2.5% of the suspension) and toluene is the continuous phase. The purpose of the water phase in the method of the '377 patent is to collect ammonium chloride, which is a byproduct of the amination reaction and which has a tendency to be occluded in the TATB if water is not so employed. Thus, the method of the '377 patent is primarily directed to producing TATB which is free of ammonium chloride. The prior art method is also distinguished in that the dispersed water phase is only a small fraction of the total reactant volume.

The present method is preferably conducted using an emulsion containing between approximately 50 and 75% by volume water, with the remainder preferably consisting of toluene.

An anionic emulsifying agent is preferably used to form the emulsion. Various emulsifiers may be used for this purpose, the only limitation being that the emulsifier be chemically stable and effective under the alkaline conditions of the amination reaction. A preferred emulsifier is ammonium oleate, which can be formed in situ during the amination reaction from oleic acid.

A protective colloid is used to stabilize the size of the dispersed droplets and protect them from agglomeration. Polyvinyl alcohol is suitable for this purpose.

EXAMPLE 1

A demonstration of the method was conducted in an 8-liter stainless steel reaction vessel which was equipped for agitation and the addition of ammonia. To the vessel was added a solution consisting of 288 grams of TCTNB, 12 milliliters of oleic acid, and 2.4 liters of toluene. To this solution was added a solution consisting of 2.7 liters of water, and 0.12 liters of a 4% solution of polyvinyl alcohol in water. The resulting emulsion mixture was agitated and gaseous ammonia was introduced at a pressure of 25 psig from a regulated source. The reaction vessel was cooled to maintain the mixture at a temperature of between 25° and 34° C. The system pressure was allowed to gradually increase to the ammonia supply pressure of 25 psig over a period of one hour. The ammonia supply was then terminated and the system was lightly agitated for another hour. The mixture was then discharged from the reaction vessel and filtered to collect the solid TATB precipitate, which was washed with water several times, reslurried in acetone, filtered and air dried. The product TATB weighed 198 grams, representing a yield of 96%. The TATB product was found to consist of uniform dendritic rosettes approximately 5 microns in diameter and 1 micron thick, having a surface area of 3.85 $m^2/g$ (BET), and containing approximately 0.08% inorganic chloride as impurity.

EXAMPLE 2

In another demonstration of the method, a solution consisting of 15.8 grams of TCTNB dissolved in 140 milliliters of toluene was placed in a 0.5 liter pressurizable reaction vessel. To this solution was added 200 milliliters of water containing 1.0 gram of the anionic emulsifier sodium lauryl sulfate, and 4.0 milliliters of a 10% water solution of polyvinyl alcohol, a protective colloid. The resulting solution was vigorously agitated and gaseous ammonia was introduced from a 40 psig regulated source. The solution and vessel were cooled to maintain the reaction temperature between 35° and 40° C. for a reaction period of approximately one hour. The resulting TATB product was recovered with a 98% yield. The product consisted of acicular crystals having a measured surface area of 2.4 $m^2/g$, and with impurities in the form of inorganic chlorides of not greater than 0.04%.

EXAMPLE 3

In another demonstration run, the same reaction conditions as set forth in Example 2 above were employed, except that 1.0 milliliters of oleic acid were substituted for the 1.0 gram of sodium lauryl sulfate used in Example 2. The resulting TATB product recovery was approximately 97%. The TATB was in the form of dendritic rosettes having a measured surface area of 3.15 $m^2/g$, with a total impurity as inorganic chloride of approximately 0.03%.

The preferred embodiment and representative examples of the method of the invention have been described above in order to explain the principles of the invention and its practical application, and in order to enable those of ordinary skill in the art to practice the invention. Various alterations, substitutions and modifications of the method described above may be made without departing from the spirit of the invention. Accordingly, the scope of the invention is defined by the following claims.

I claim:

1. A method of forming fine-grained sym-triaminotrinitrobenzene (TATB) comprising the amination of 1,3,5-trichloro-2,4,6-trinitrobenzene (TCTNB) in an emulsion of toluene in water that contains a protective colloid consisting essentially of polyvinyl alcohol and an emulsifying agent, wherein the volume of water in said emulsion is greater than the volume of said toluene, such that the water is the continuous phase and the toluene is the dispersed phase in the emulsion.

2. The method defined in claim 1 wherein said amination is conducted by introducing gaseous ammonia into said emulsion.

3. The method defined in claim 2 wherein said gaseous ammonia is introduced at a pressure of between approximately 20 and 45 psig.

4. The method of claim 2 wherein said amination is conducted in a pressurizable reaction vessel, and wherein said gaseous ammonia is introduced so as to increase the reaction pressure from atmospheric pressure to between approximatey 20 and 45 psig over a period of approximately one hour.

5. The method of claim 1 wherein said emulsifying agent consists essentially of ammonium oleate.

6. The method defined in claim 2 wherein said emulsifying agent consists essentially of ammonium oleate formed in situ by the reaction of oleic acid with said ammonia introduced into said emulsion.

7. The method defined in claim 1 wherein said polyvinyl alcohol is present at a concentration of at least 1.5 g/liter of organic solvent.

8. The method of claim 1 wherein said amination is conducted at a temperature of between 25° and 40° C.

* * * * *